United States Patent
Vastola et al.

(12)

(10) Patent No.: US 10,448,870 B2
(45) Date of Patent: Oct. 22, 2019

(54) PULSE OXIMETER SENSOR

(71) Applicant: WRISTDOCS LLC, Lebanon, TN (US)

(72) Inventors: Mark Vastola, Lebanon, TN (US); Jacob Conner, Strafford, MO (US); Kevin Whitworth, Ozark, MO (US); Ryan Woolsey, Springfield, MO (US)

(73) Assignee: WristDocs LLC, Lebanon, TN (US)

( * ) Notice: Subject to any disclaimer, the term of this patent is extended or adjusted under 35 U.S.C. 154(b) by 876 days.

(21) Appl. No.: 14/892,661

(22) PCT Filed: Dec. 12, 2013

(86) PCT No.: PCT/US2013/074528
§ 371 (c)(1),
(2) Date: Nov. 20, 2015

(87) PCT Pub. No.: WO2014/189545
PCT Pub. Date: Nov. 27, 2014

(65) Prior Publication Data
US 2016/0100780 A1    Apr. 14, 2016

Related U.S. Application Data

(60) Provisional application No. 61/825,198, filed on May 20, 2013.

(51) Int. Cl.
*A61B 5/1455* (2006.01)
*A61B 5/00* (2006.01)
*A61B 5/02* (2006.01)

(52) U.S. Cl.
CPC ........ *A61B 5/14552* (2013.01); *A61B 5/0002* (2013.01); *A61B 5/6825* (2013.01);
(Continued)

(58) Field of Classification Search
None
See application file for complete search history.

(56) References Cited

U.S. PATENT DOCUMENTS 5,090,410 A * 2/1992 Saper ................. A61B 1/00142
356/41
5,425,360 A * 6/1995 Nelson ............... A61B 5/14552
356/41
(Continued)

FOREIGN PATENT DOCUMENTS

EP    0357249 B1    7/1994
EP    0992214 B1    1/2005
(Continued)

OTHER PUBLICATIONS

International Search Report and Written Opinion from International Application No. PCT/US2013/074528, entitled "Pulse Oximeter Sensor," dated Feb. 14, 2014.

*Primary Examiner* — Eric F Winakur
*Assistant Examiner* — Marjan Fardanesh
(74) *Attorney, Agent, or Firm* — DT Ward, PC; Donna T. Ward; Christopher P. Sullivan

(57) ABSTRACT

The invention provides a pulse oximetry sensor for attachment to the lower half of the palm or the ulnar edge of the palm. The sensor may be portable, untethered and in some instances, disposable. The features of the sensor make it effective in stable, chronic or emergency medical settings.

13 Claims, 17 Drawing Sheets

(52) U.S. Cl.
CPC ............ *A61B 5/6832* (2013.01); *A61B 5/742* (2013.01); *A61B 5/02* (2013.01)

(56) References Cited

U.S. PATENT DOCUMENTS

| | | | |
|---|---|---|---|
| 2002/0038082 A1 | 3/2002 | Chin | |
| 2005/0209514 A1* | 9/2005 | Oshima | A61B 5/14532 600/310 |
| 2009/0108205 A1* | 4/2009 | Duffy | A61B 5/14552 250/339.07 |
| 2009/0326354 A1* | 12/2009 | Mao | A61B 5/14532 600/344 |
| 2012/0165630 A1 | 6/2012 | Knight et al. | |
| 2013/0079609 A1 | 3/2013 | Besko | |

FOREIGN PATENT DOCUMENTS

| | | | |
|---|---|---|---|
| WO | 2005023097 A2 | 3/2005 | |
| WO | 2006005169 A1 | 1/2006 | |
| WO | 2006123098 A2 | 11/2006 | |

* cited by examiner

PULSE OXIMETER SENSOR

CROSS REFERENCE TO RELATED APPLICATIONS

This application is a 35 U.S.C. § 371 U.S. National Stage Entry of International Application No. PCT/US2013/074528 filed Dec. 12, 2013, entitled Pulse Oximeter Sensor, which claims the benefit of priority of US Provisional Patent Application No. 61/825,198 filed May 20, 2013, entitled Pulse Oximeter Sensor, the contents of which are each incorporated herein by reference in its entirety.

FIELD OF THE INVENTION

The present invention is in the field of biotelemetry sensors and systems and more specifically, pulse oximetry sensors and systems.

BACKGROUND OF THE INVENTION

Biotelemetry is the process of measuring biometric data. Telemetry systems in the art have traditionally been focused on the multi-measurement and monitoring of biological statistics and have been tethered to large monitoring systems.

The present invention provides a pulse oximetry sensor and system focused on improvement at the "point of care" including improvements in portability, functionality and efficiency.

SUMMARY OF THE INVENTION

The present invention provides a pulse oximeter sensor for attachment to the lower half of the palm or the ulnar edge of the palm A pulse oximeter is a non-invasive medical device for measuring oxygenation of the blood. Oximetry involves the use of two light sources having differing wavelengths (usually red at about 600 nm and infrared at about 900 nm). The light sources are sequentially passed through the patient's body or a portion of a patient's body to a detector. The difference in absorbance of each of the two wavelengths is measured, allowing determination of the net absorbance as altered by the pulse of arterial blood. The ratio of absorbance between the red and infrared light caused by the variance between oxygenated and un-oxygenated blood (or hemoglobin status) is an indirect measure of the percent of hemoglobin molecules bound with oxygen molecules.

A majority of pulse oximeters currently available on the market suffer from lack of a secure fit because they are primarily attached via a clip to the fingertip. Alternative sensor placement is possible and has been reported for the toe, nose, forehead and ball of the foot. Wrist oximeters are known in the art. Most of these, however, are limited to the display module worn on the wrist like a wristwatch but with the sensor still placed on the tip of the finger and tethered to the wrist band display. Pulse oximeters worn on the wrist with alternative placement of sensors, such as the sensor described in International Patent Application No. WO2013030744 are also expected to suffer from problems arising due to relative motion of the dorsal part of the hand with respect to the wrist, which can cause alterations in signals obtained from the sensors. Upward motion of the hand from a resting position, for example, is one type of motion which can disturb readings obtained from a pulse oximeter sensor placed on the wrist because the base of the hand above the wrist crease impacts the edge of a wristwatch-type sensor.

The present inventors have recognized the need for a pulse oximeter sensor that can be worn on the hand at a position relatively free from motions that interfere with the sensor signals, particularly motions involving wrist flexion and curling of fingers in the process of gripping. The present invention addresses this need, among others which will be discussed herein below.

In accordance with one aspect of the present invention, there is provided a pulse oximetry sensor assembly for attachment to the lower half of the palm or the ulnar edge of the palm, the sensor assembly comprising: a) an elongate body supporting a light emitting source and a detector for detecting scattered light originating from the light emitting source, wherein the light emitting source and the detector are configured to detect scattered light from a surface of the lower half of the palm or the ulnar edge of the palm; and b) a means for transmitting signals corresponding to the scattered light acquired by the detector to a signal processing unit.

Another aspect of the invention provides a pulse oximetry system comprising: a) the pulse oximetry sensor assembly described herein; b) a transmission cable as the means for transmitting signals acquired by the detector, the transmission cable in electrical communication with the detector; and c) a signal processing unit in electrical communication with a display unit for displaying pulse oximetry readings.

Another aspect of the invention provides a kit comprising the sensor assembly described herein and instructions for attachment of the sensor assembly to the lower half of the palm or the ulnar edge of the palm.

Another aspect of the invention is a method for obtaining pulse oximetry readings, the method comprising the steps of: a) attaching a pulse oximetry sensor to the palmar side of the ulnar edge of the palm between the wrist crease and the base of the fifth digit, substantially parallel to a longitudinal axis defined by the fifth digit; b) connecting the sensor to a signal processing unit; and c) reading output data from the signal processing unit.

Another aspect of the invention is a method for obtaining pulse oximetry readings, the method comprising the steps of: a) attaching a pulse oximetry sensor to the palmar side of the ulnar edge of the palm adjacent the wrist crease and substantially parallel to a transverse axis defined by the pisiform, lunate and scaphoid carpal bones; b) connecting the sensor to a signal processing unit; and c) reading output data from the signal processing unit.

Another aspect of the invention is a method for obtaining pulse oximetry readings, the method comprising the steps of: a) attaching a pulse oximetry sensor to the of the ulnar edge of the palm substantially parallel to the longitudinal axis formed by the fifth digit; b) connecting the sensor to a signal processing unit; and c) reading output data from the signal processing unit.

Another aspect of the invention is a method for obtaining pulse oximetry readings, the method comprising the steps of: a) attaching a pulse oximetry sensor to the lower half of the palm and substantially parallel to an axis defined by the scaphoid and trapezoid carpal bones and the first digit; b) connecting the sensor to a signal processing unit; and c) reading output data from the signal processing unit.

BRIEF DESCRIPTION OF THE DRAWINGS

In FIG. 15A, the sensor assembly 1000 is connected to a signal processing unit 1130 by a transmission cable 1080 which has plugs 1084 and 1086 for attachment and detachment of the transmission cable 1080. The signal processing unit 1130 also has connections to a computer 1140 and a removable data storage unit 1150. In FIG. 15B, the system is similar to that of FIG. 15A except that the sensor is connected to a wireless transmitter 1172 for transmitting a signal 1170 from the sensor to a wireless receiver 1174.

DETAILED DESCRIPTION

Figure 1:
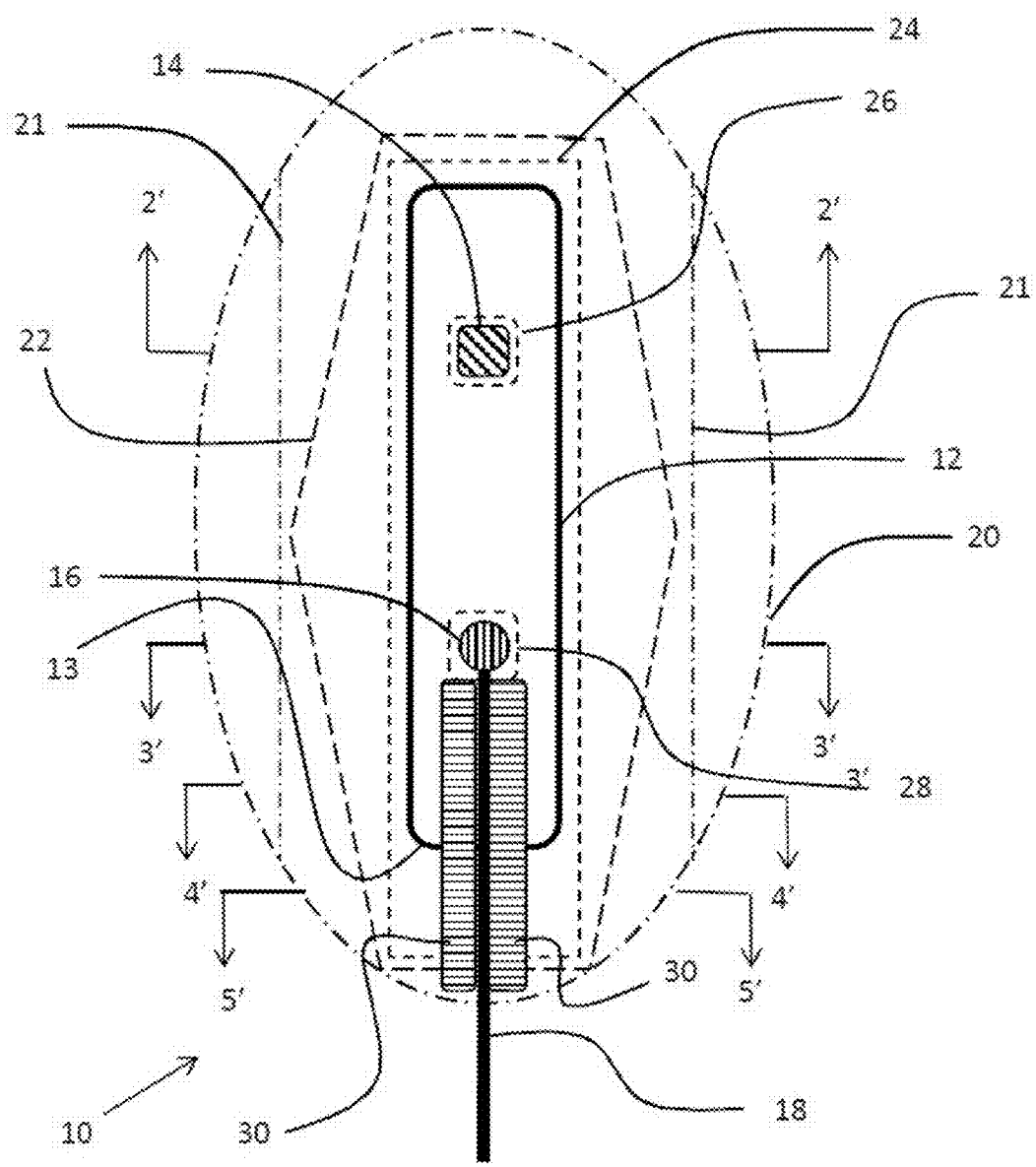
FIG. 1 is a schematic transparent top view of the pulse oximeter sensor assembly 10 of one particular embodiment of the present invention which includes a cover film 20, a protective pad 22 and a skin protecting pad 24.

The present invention provides a pulse oximetry sensor, as well as a system and kit comprising the sensor. The present invention also provides a method for obtaining pulse oximetry readings from the lower half of the palm or the ulnar edge of the palm. The pulse oximetry sensor of various embodiments of the present invention may be used with subjects of all ages from infants, including premature infants, pediatric patients, adults and the elderly. The system may comprise features which help in the subject's comfort, mobility, and ease of use such as, but not limited to, hypoallergenic materials, flexible materials, size and shape options of the system, and the ability for the sensor to expand in order to accommodate swelling.

The system may further comprise features of being disposable and modular. The pulse oximetry sensor of the present invention may be wireless (portable) and may be battery supported. Where a battery is employed it is advantageous for the system to operate for long periods of time. When data from the system are sent to a monitor, the reports produced may have the capability of producing graphs of prolonged data streams or instant readouts. Monitors and graphing devices are well known in the art and can be used in conjunction with the pulse oximeter system of the present invention.

The pulse oximeter sensor of the present invention has multiple uses in healthcare. Non-limiting examples of uses for inpatient monitoring include hospitals such as pediatric hospitals, assisted living facilities, nursing homes, rehabilitation facilities, intensive care units, respiratory departments, cardiac care centers, emergency departments and other specialized areas in medical facilities. In a further embodiment, the pulse oximeter of the present invention may be manufactured to be worn by a subject for extended periods of time and will have optional features such as a skin protection pad for minimizing discomfort. The system may also be employed in the field in settings such as for example in military applications where soldiers are often separated from direct healthcare providers. In this situation, the portable modular nature of the sensor allows for inclusion of the pulse oximeter system in a standard first aid kit and may be easy enough to employ that any lay person can immediately attach it to an injured person and activate the system.

Certain embodiments of the pulse oximeter system may also provide information directly to the subject or to a user in the vicinity of the subject. The subject or the user may trigger the system to gather or provide information on the subject at a particular instance. In this case, the subject or the user would have access to an identifier button on the device that can be pushed to log a specific instance of a physical symptom. When the identifier button is pushed, information such as, but not limited to, the subject's vital statistics, the date and the time may also be recorded so that the information can be assessed to determine if there was a change in health status.

The modular nature of the sensor affords the health care professional the option of removing the sensor and replacing it with a new sensor. This aspect of the invention also aids in the reduction of nosocomial infections and the spread of microorganisms under unsterile conditions.

Depending on the intended use, the pulse oximetry sensor may be used as part of a system configured to record, save, and upload historical data for clinical studies and patient information documentation. The system may be employed passively to measure vital statistics over a period of time or may be triggered by an event or situation which captures one or more metrics for storage or relay to a remote location. In this manner, the condition of a patient may be monitored for gradual or instant changes in biometrics which can signal to the patient or to a healthcare provider that one or more treatment regimens are needed.

Embodiments of the present invention will now be described with reference to the drawings. A number of features that may be incorporated into alternative embodiments will be described during the course of the description of the example embodiments. The skilled person will recognize that these alternative embodiments are also within the scope of the invention. Similar reference characters refer to similar parts throughout the different views. The drawings are not necessarily to scale and emphasis is instead placed upon illustrating the principles of this particular embodiment and other aspects of the invention.

Features of a First Embodiment of the Sensor Assembly

Referring now to FIGS. 1-5 there is shown an embodiment of a pulse oximetry sensor assembly shown generally at 10. Sensor assembly 10 includes an elongated body 12 which in some embodiments may be formed of rigid plastic or other relatively rigid material appropriate for use as a substrate for a medical sensor. In other embodiments, the elongated body is not rigid and may be provided by a length of tape, as described hereinbelow. In embodiments where a substantially rigid body is provided, examples of plastics appropriate for constructing the body 12 include, but are not limited to, polyethylene, polypropylene, polystyrene, polyester, polycarbonate, polyvinylchloride, nylon, poly(methyl methacrylate) and the like. The body 12 may be biodegradable and/or may be superabsorbent. These features are particularly advantageous in embodiments when the sensor assembly 10 is intended to be for single use and disposable. In various embodiments, the body 12 may have different lengths and widths which may be selected according to the size of the hand of the individual for whom pulse oximetry measurements are desired. For example, a sensor body 12 may be constructed for pediatric use which will have shorter lengths and widths. In such pediatric uses, alternative placements of the sensor assembly may be applicable, particularly for infants who may require placement of the sensor assembly on a transverse or longitudinal position of the foot, such as the heel, which is expected to provide similar light scattering characteristics as the lower half of the palm or the ulnar edge of the palm. Additionally, a sensor body 12 of a sensor assembly 10 constructed to fit an adult male may be longer and wider than a sensor intended for use by an adult female. In various embodiments of the present invention therefore, the length of the body 12 may range between about 30 mm to about 75 mm and range in width between about 8 mm to about 15 mm. As used herein, the term "about" indicates a variation of plus or minus 10% of the value indicated.

A light emitting source 14 is supported by the body 12. The support provided by the body 12 may be provided by a housing, compartment or other such arrangement on or in the body or, alternatively, the light emitting source 14 may simply rest upon the body 12. In certain embodiments, the light emitting source 14 is a light emitting diode (LED). Other embodiments may use other types of light emitters which are known to those skilled in the art. In certain embodiments of the invention, the LED is a bi-color LED which emits light at both 600 nm and 900 nm for example, an LED with part number SMT660/910 which is commercially available from Epitex Inc. of Kyoto, Japan. Other LEDs suitable for use with the present invention are manufactured by Hamamatsu Photonics (Hamamatsu, Japan—part numbers L5276, L5586, and L6286) and by OSI Optoelectronics Inc. (Hawthorne, Calif., USA); DLED-660/880-LLS-2 64/Leadless Ceramic 2 Leads/Back to Back, DLED-660/895-LLS-2 895, DLED-660/905-LLS-2 905, DLED-660/905-LLS-3 905 3 Leads/Common Anode, DLED-660/940-LLS-3 940, DLED-660/880-CSL-2 880 63/Side Locker Plastic, DLED-660/895-CSL-2 895 2 Leads/Back to Back, DLED-660/905-CSL-2 905, DLED-660/905-CSL-3 905 3 Leads/Common Anode, and DLED-660/940-CSL-3. Other LEDs are known to the skilled person and these other LEDs may also be suitable for use as light emitting sources in alternative embodiments. The person skilled in the art knows how to configure these LEDs in combination with a sensor body such as body 12 and that this may be done without undue experimentation. The skilled person will also recognize that alternative embodiments may have two separate light emitting sources, with a first light emitting source configured to provide light for measuring light absorbance of oxygenated blood and a second light emitting source configured to provide light for measuring light absorbance of deoxygenated blood. In such alternative embodiments, both light emitting sources are housed within or supported on the body 12 at locations which may be determined by the skilled person without undue experimentation.

Figure 2:
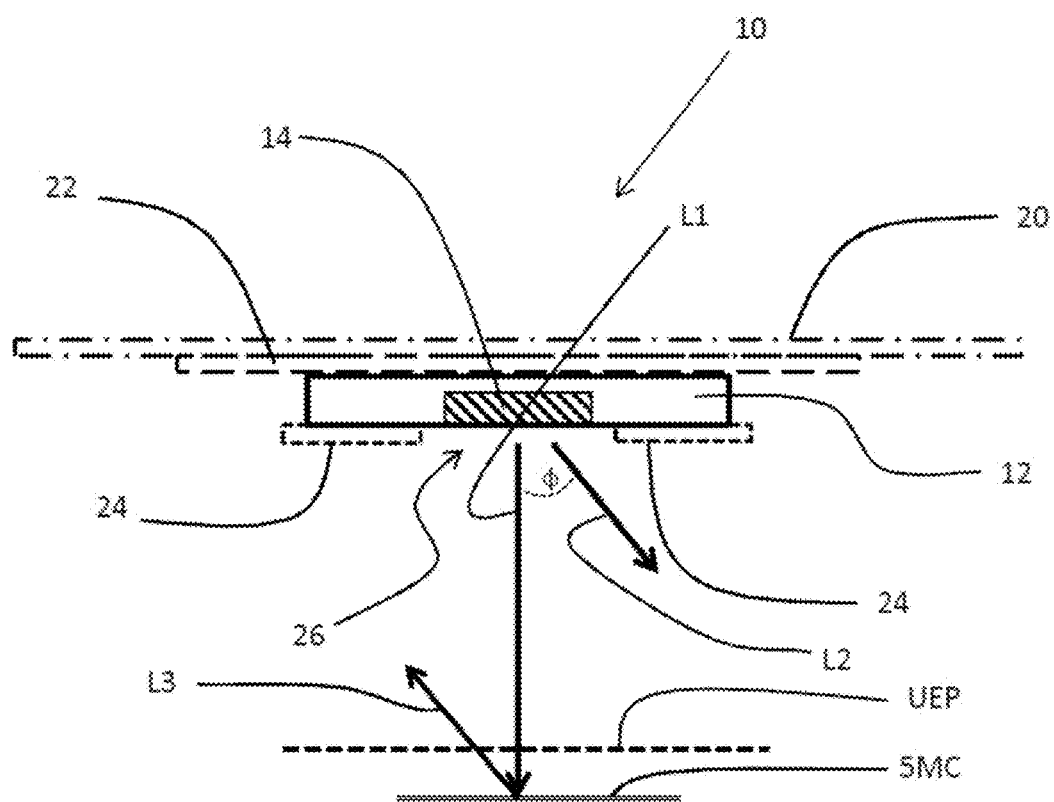
FIG. 2 is a cross sectional view taken along line 2'-2' of FIG. 1 to illustrate the levels of the cover film 20, protective pad 22 and skin protecting pad 24 with respect to the body of the sensor 12. The light emitting source 14 is also shown.

In one embodiment, the light emitting source 14 may be positioned or trained within its location in the elongate body 12 to emit light along an angled path. Such an angle is shown in FIG. 2 and represented by the symbol $\varphi$. In FIG. 2, light emitted orthogonal to the surface of the palmar side of the ulnar edge of the palm UEP is indicated by L1 and light emitted along the angled path is indicated by L2. For simplicity, only the scattering of L1 at the fifth metacarpal 5MC (for example) is shown as L3. It should be understood that L2 would also be expected to scatter from various other tissues in the lower half of the palm, particularly in the vicinity of the palmar side of the ulnar edge of the palm or the ulnar edge of the palm itself, such as, for example, epidermis, dermis, tendons, muscles (such as the abductor and flexor of the digiti minimi), blood vessels (such as the ulnar artery), synovial fluid and bones. In cases where scattering from hard bone tissue occurs as the predominant source of the scattering, the scattering is from one or more of the bones located in the lower half of the palm or the ulnar edge of the palm, such as any of the five metacarpals, and any of the carpals, including the pisiform, the scaphoid, the capitate, the trapezoid, the trapezium, the scaphoid, the triquetrum, the lunate and the hamate. The arrangements of the sensor with respect to the lower half of the palm or the ulnar edge of the palm and the bones of those locations is indicated in FIGS. 10-14 and will be described in more detail hereinbelow. The scattered light is differentially absorbed by oxygenated and deoxygenated blood vessels and it is this differential absorbance that forms the basis for pulse oximetry readings.

The body 12 also houses a detector 16 configured to detect light which is emitted from the light emitting source 14 and scattered from structures of the palmar side of the ulnar edge of the palm UEP as indicated above. In one particular embodiment, the detector is a blue enhanced PIN silicon photodiode (Part No. PDV-C173SM), which is commercially available from Advanced Photonics Inc. of Camarillo, Calif., USA. In other embodiments, the detector is a PIN-0.81-CSL 0.81 mm$^2$ PIN diode photodetector type 60 with a molded frame (OSI Optoelectronics, Hawthorne, Calif., USA). This detector is matched to a dual emitter LED. Other detectors include PIN-4.0-CSL or PIN-8.0-CSL photodetectors which are also manufactured by OSI Optoelectronics. The skilled person will recognize that other detectors may be selected and can be adapted for use with certain embodiments of the present invention without undue experimentation.

Figure 3:
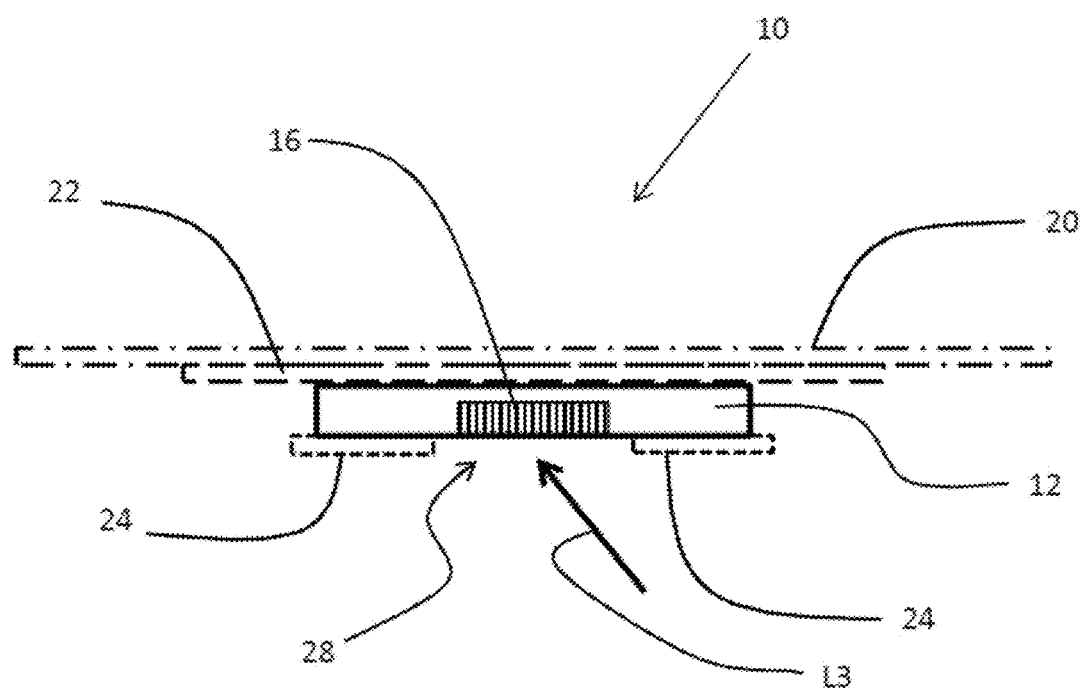
FIG. 3 is a cross sectional view taken along line 3'-3' of FIG. 1 to illustrate the levels of the cover film 20, the protective pad 22 and the skin protecting pad 24 with respect to the body of the sensor 12. The detector 16 is also shown.

It is seen in FIG. 3 that scattered light L3 travels to the detector 16 where it is converted to a signal that ultimately provides a measurement indicating the extent of oxygenation of blood.

In one embodiment, the linear distance from the center of the LED to the center of the detector is between about 8 mm to about 10 mm. In another embodiment, the linear distance from the center of the LED to the center of the detector is about 9 mm. In another embodiment, the linear distance from the center of the LED to the center of the detector is 9.16 mm.

Figure 15:
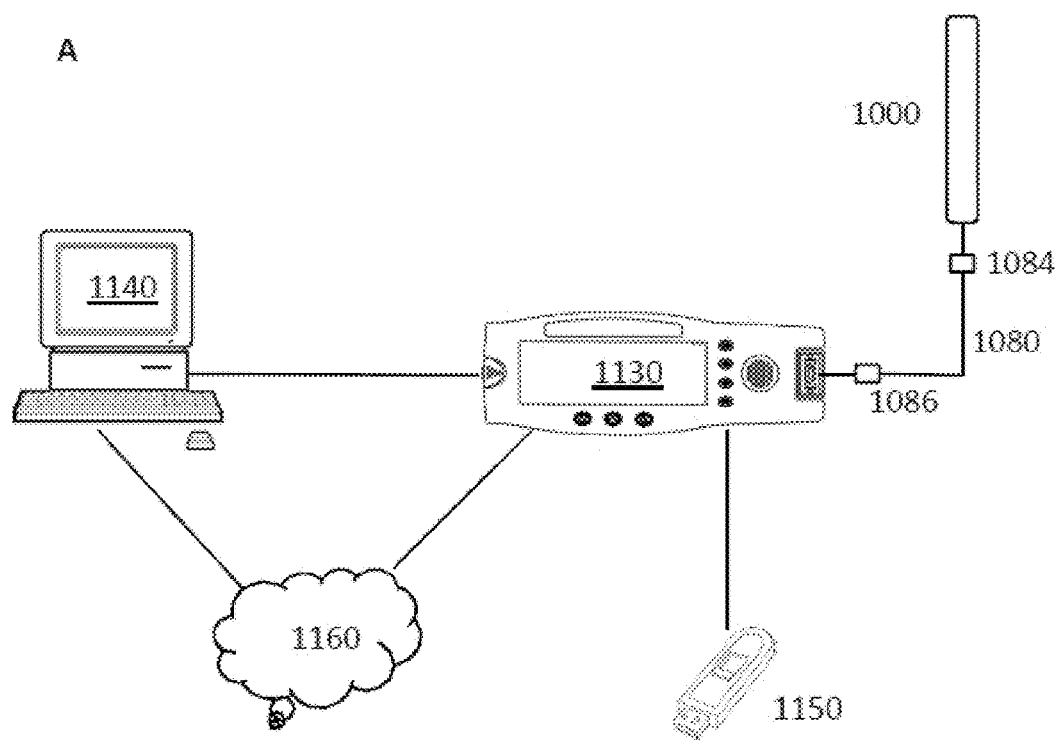
FIGS. 15A and 15B show system diagrams according to two embodiments of a pulse oximetry system.
Figure 15:
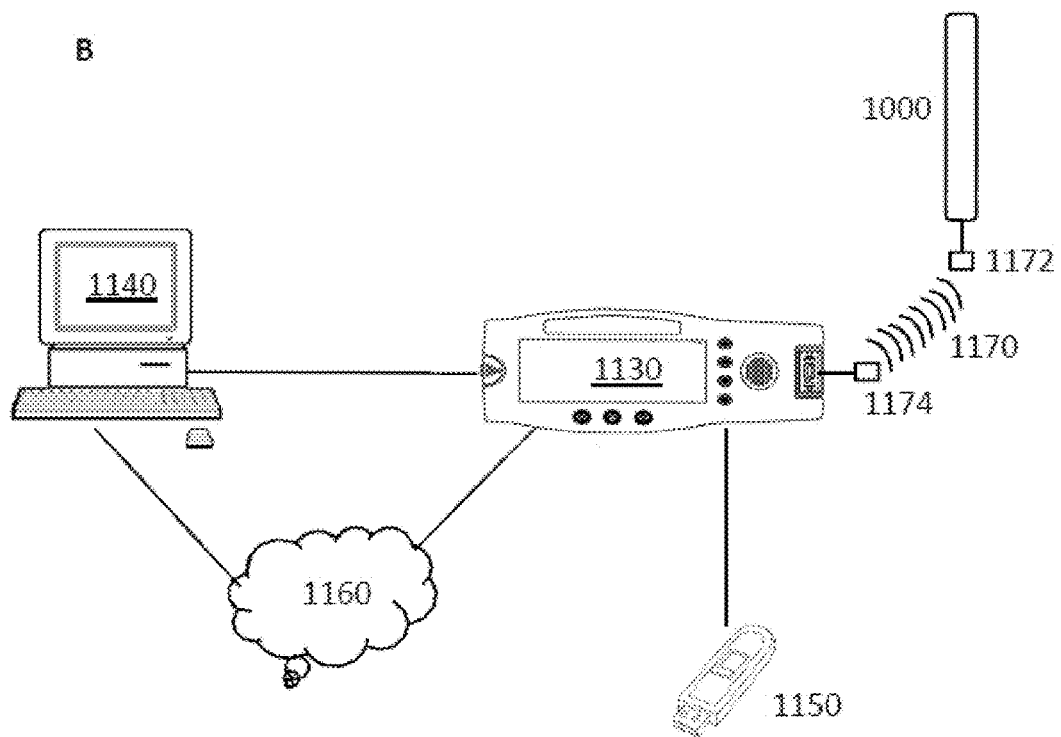
Figure 16:
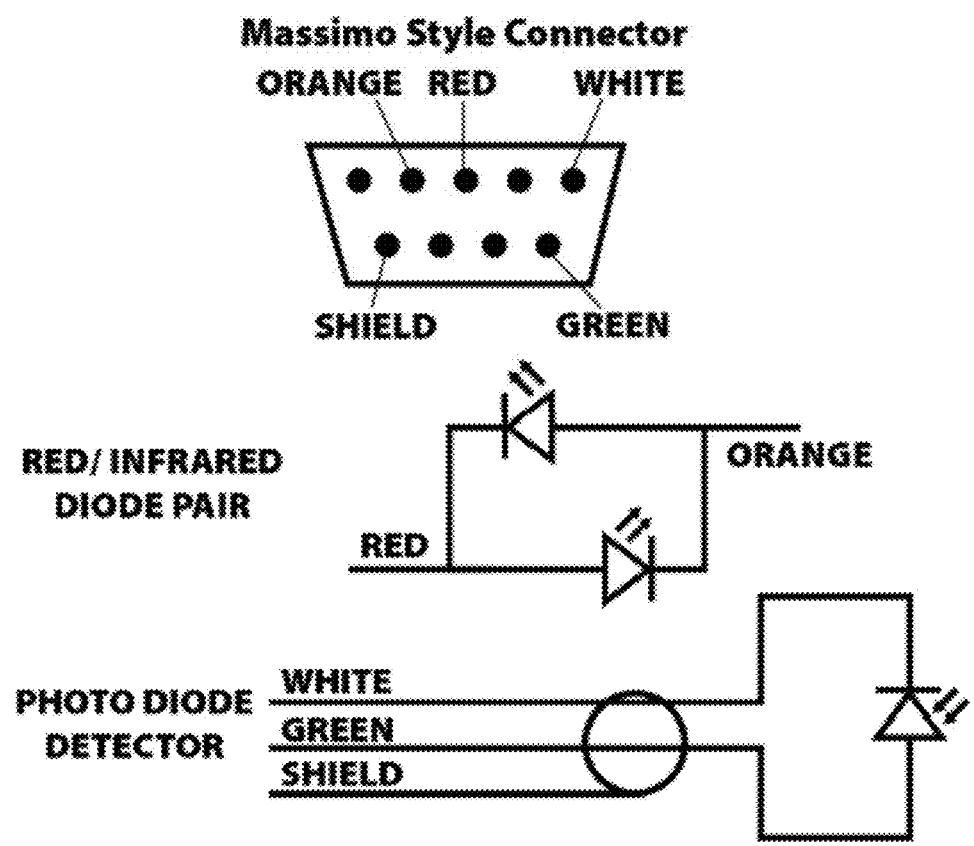
FIG. 16 is a schematic diagram showing circuit details of a MASSIMO™ connector, a red/infrared diode pair and a photo diode detector.
Figure 17:
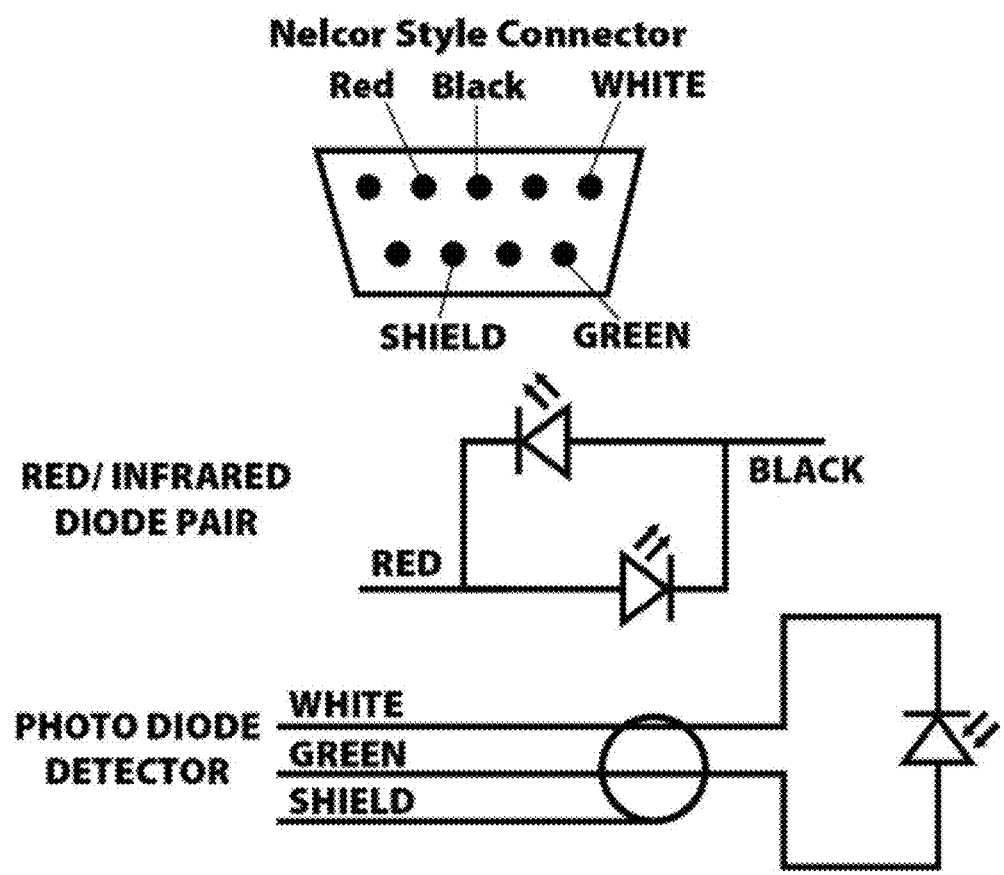
FIG. 17 is a schematic diagram showing circuit details of a NELLCOR™ connector, a red/infrared diode pair and a photo diode detector.

With reference to FIG. 1, it can be seen that the detector 16 is connected to a transmission cable 18 for transmission of signals obtained from the detector 16 which indicates the extent of light absorbance of deoxygenated and oxygenated blood. The skilled person will recognize that the light emitting source requires a source of electrical power. For the sake of clarity, this is not shown in FIGS. 1-5 but the skilled person will recognize that electrical power can be transmitted to the light emitting source by wires residing in the transmission cable 18 and running across the body 12 to the light source 14. The signals obtained at the detector 16 are transmitted through transmission cable 18 to a signal processing unit (not shown in FIG. 1). The transmission cable 18 may also hold the wires that provide electrical power to the light emitting source 14. In two particular embodiments, transmission cable 18 is provided with a 9-pin MASSIMO™ plug (as shown in FIG. 16) for connection to a MASSIMO™ monitor or is provided with a 9-pin NELLCOR™ plug (as shown in FIG. 17) for connection to a NELLCOR™ monitor. In certain alternative embodiments, the transmission cable 18 is detachable from the body 12 (see also the system diagram in FIG. 15A which will be described in more detail hereinbelow). Such alternative embodiments are particularly advantageous when the sensor assembly 10 is intended to be disposable because the transmission cable 18 can be saved while the sensor assembly 10 is discarded after use. As an alternative to a transmission cable 18, a wireless signal transmission system may be incorporated into sensor assembly 10 and its associated signal processing unit (see FIG. 15B). Such wireless systems, such as Bluetooth, are well known to the skilled person and may be adapted for use with certain embodiments of the present invention without undue experimentation.

The particular embodiment of the sensor of the invention shown in FIG. 1 includes layers of adhesive material and protective padding. The skilled person will recognize that these features do not affect the general sensing functions of the sensor assembly 10 and are provided to improve the practicalities associated with attachment of the sensor assembly 10 to the lower half of the palm or the ulnar edge of the palm UEP, such as protection of the sensor assembly 10 from external impacts and protection of the skin of the lower half of the palm or the ulnar edge of the palm UEP to minimize discomfort. The relationships between these features with respect to the sensor body 12 are indicated in FIG. 1 and are also shown more clearly in cross sectional view in FIGS. 2-5 (indicated by cross section lines 2'-2', 3'-3', 4'-4' and 5'-5' of FIG. 1). In various embodiments, these layers of adhesive materials and padding may be omitted from the construction of the sensor and replaced by materials which may be available in various healthcare settings, such as gauze pads, bandages, medical grade tape and the like.

It can be seen in FIGS. 1-5 (wherein FIG. 1 which provides a transparent top view of all layers), that a hexagonal-shaped protective pad 22 is provided over the top surface of the sensor body 12. Rectangular or oval-shaped protective pads may also be used. The function of protective pad 22 is simply to protect the sensor body 12 from external impacts. The materials used in the construction of such a protective pad 22 are commercially available and are well known to the skilled person. In certain embodiments, the protective pad 22 has a length of about 30 mm to about 75 mm and a width of about 10 mm to about 33 mm. In certain embodiments, the length is 65 mm. In certain embodiments, the width is 30 mm. In some embodiments, the length is 65 mm and the width is 30 mm.

Affixed to the top surface of the protective pad 22 is a cover film 20 which provides the function of fixing the sensor assembly to the lower half of the palm or the ulnar edge of the palm UEP. The cover film 20 is shown with an oval-shaped dot-dashed line in FIG. 1. It is seen in the cross-sectional views of FIGS. 2-5 that the protective pad 22 is sandwiched between the cover film 20 and the top surface of the sensor body 12. The oval shape of the cover film 20 may be substituted for other shapes in alternative embodiments. In certain embodiments, the cover film 20 may be constructed of elastomeric plastic material such as elastomeric polyurethane, for example. The cover film 20 is coated with a suitable adhesive material for fixing the cover film 20 to the skin. Adhesives suitable for use with this elastomeric plastic material are medical grade acrylic adhesives or synthetic rubber-based adhesives which are well known to the person skilled in the art. Acrylic (or acrylate) adhesive has proven compatibility with skin and offers a range of performance characteristics and adhesion profiles. These types of adhesives have low sensitization potential and are convenient for use in manufacturing processes. Some examples of commercially adhesive film materials which may be adapted for use as adhesive films of certain embodiments of the present invention include the materials used in transparent film medical dressings such as 3M Tegaderm™ and Opsite Flexifit™ (Smith & Nephew, Memphis, Tenn., USA), the latter of which is waterproof and provides resistance to growth of bacteria as well as minimizing the risk of skin damage upon removal. A series of medical dressings formed of various plastics and provided with medical grade adhesives, some of which are formed of materials appropriate for use in forming the cover film 20 in various embodiments of the present invention, are described on the internet site www.dressings.com (the content of which is incorporated herein by reference in entirety). This internet site is maintained by the Surgical Dressing Manufacturer's Association (Chesterfield, UK). The skilled person has the knowledge to select such commercially-available dressings from this list for use as adhesive films in various embodiments of the present invention. Such selections may be made by the skilled person without undue experimentation.

In certain embodiments, the cover film 20 has a length ranging between about 75 mm to about 95 mm at its longest point and a width of about 40 mm to about 75 mm at its widest point. In certain embodiments the width of the cover film 20 is 60 mm. In certain embodiments, the length of the cover film 20 is 90 mm. In certain embodiments, the length and width of the cover film 20 are 90 mm and 60 mm, respectively.

In certain embodiments, the cover film 20 is provided with backing paper (not shown) to protect the adhesive surface of the cover film 20 prior to use. As indicated in FIG. 1, outer edges of the cover film 20 are defined by lines 21 and the backing paper covering these outer edges is non-adhesive peel paper which is easier to remove than the backing paper covering the remainder of the cover film 20. Once the non-adhesive peel paper is removed, the remaining backing paper can then be easily removed from the cover film 20 without causing wrinkling of the cover film 20.

Figure 4:
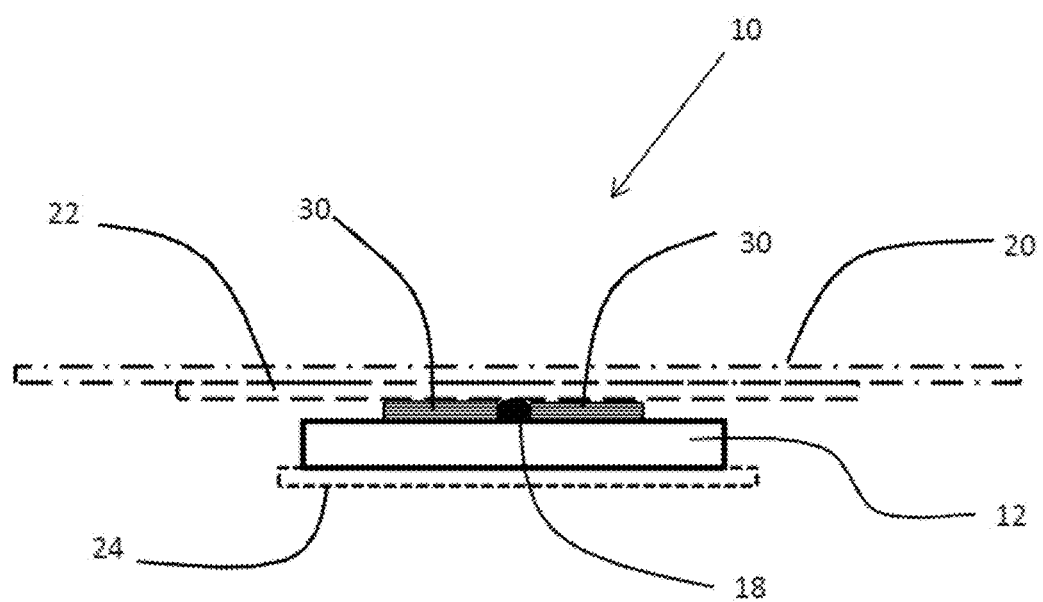
FIG. 4 is a cross sectional view taken along line 4'-4' of FIG. 1 to illustrate the levels of the cover film 20, the protective pad 22 and the skin protecting pad 24 with respect to the body of the sensor 12. The transmission cable 18 and the adhesive resin 30 are also shown.
Figure 5:
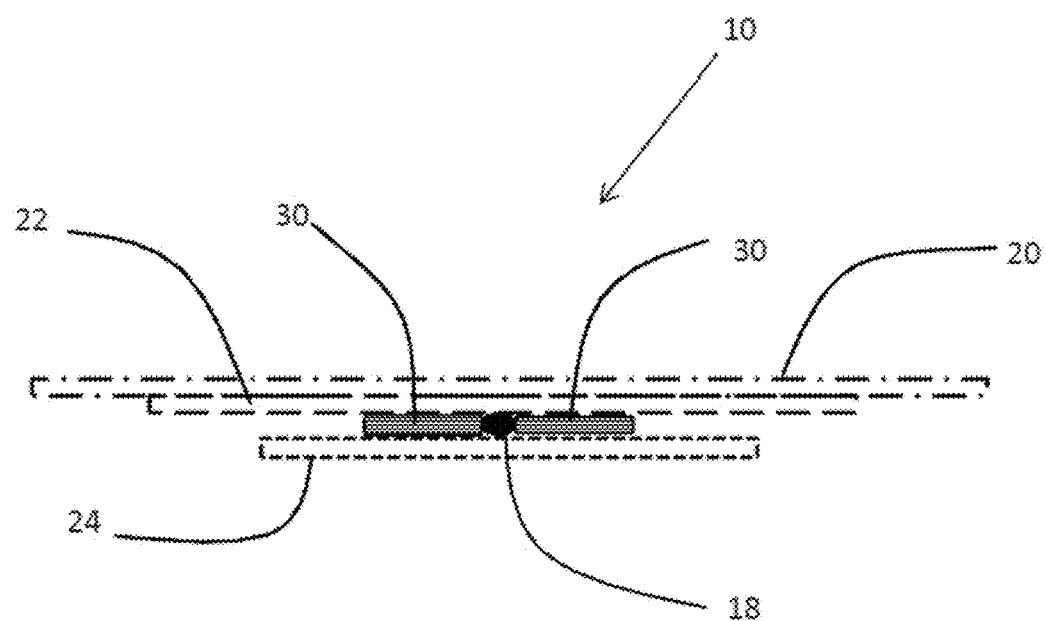
FIG. 5 is a cross sectional view taken along line 5'-5' of FIG. 1 to illustrate the levels of the cover film 20 and the protective pad 22 with respect to the transmission cable 18 and the adhesive resin 30.

It may also be seen in FIG. 1, and in the cross-sectional views of FIGS. 4 and 5, that the protective pad 22 and the cover film 20 also hold the transmission cable 18 in place outside the proximal end 13 of the body 12. In this embodiment, additional reinforcement of the transmission cable 18 is provided by an extra adhesive film 30 such as a Scapa silicone adhesive pad (Scapa, Windsor, Conn., USA) or 3M Tegaderm™ adhesive polymer film disposed on each side of the transmission cable 18. The extra adhesive film 30 may also be added between the top of the transmission cable 18 and the lower surface of the protective pad 22. An appropriate adhesive film 30 may be selected from various commercially available adhesive films which are compatible with medical uses. In alternative embodiments, other means for fixing the transmission cable 18 in place may be used in place of the adhesive film 30 (such as glues or other types of adhesive resins which are known to those skilled in the art).

As seen in FIGS. 1-5, in this particular embodiment, a skin protecting pad 24 is affixed to the bottom surface of the body 12. The skin protecting pad 24 may be constructed of medical grade polymers, woven or non-woven cloths or fabrics or films provided with hypoallergenic silicone adhesives such as the adhesives used in Scapa pads or Tegaderm™ pads or other similar material suitable for protection of the skin from possible irritations caused by contact with the body 12 and for prevention of trapping of heat against the ulnar surface of the palm. The skin protecting pad 24 is provided with openings 26 and 28 which allow passage of light from the light emitting source 14 and to the detector 16, respectively. The skin protecting pad 24 generally prevents contact of the skin with the sensor body 12 and with the transmission cable 18 extending from the proximal end 13 of the sensor body 12.

In certain embodiments, the detector 16 is provided with a layer of insulating tape (not shown) for shielding the electronic components from electromagnetic interference. In certain embodiments, the shielding tape is disposed between the body 12 and the protective pad 22.

Features of a Second Embodiment of the Sensor Assembly

Figure 6:
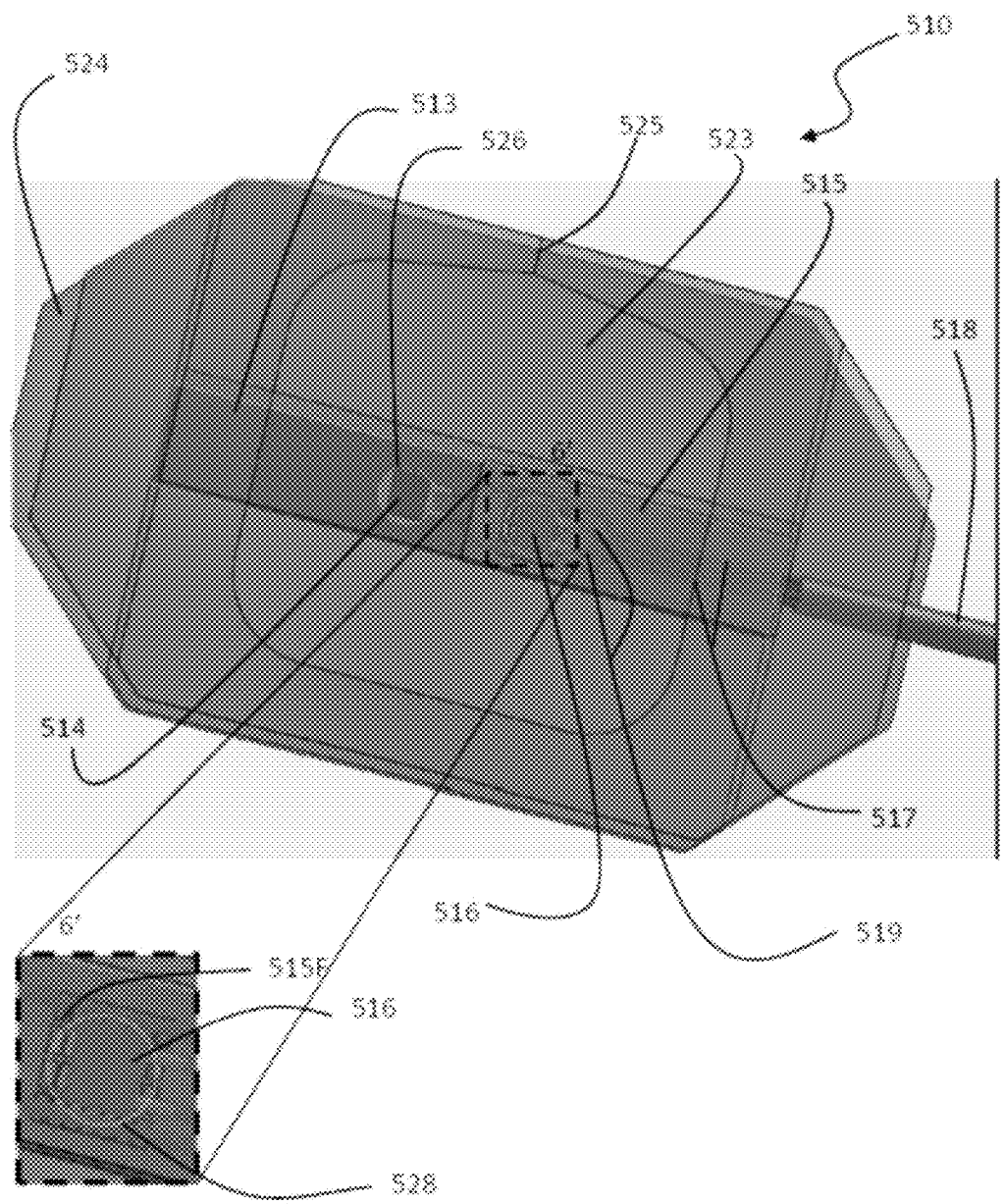
FIG. 6 is a semi-transparent top view of another embodiment of the sensor assembly 510 which includes a skin-contacting film 524, a cover film 520 and a radiofrequency/electromagnetic interference shield 515 covering the detector.
Figure 7:
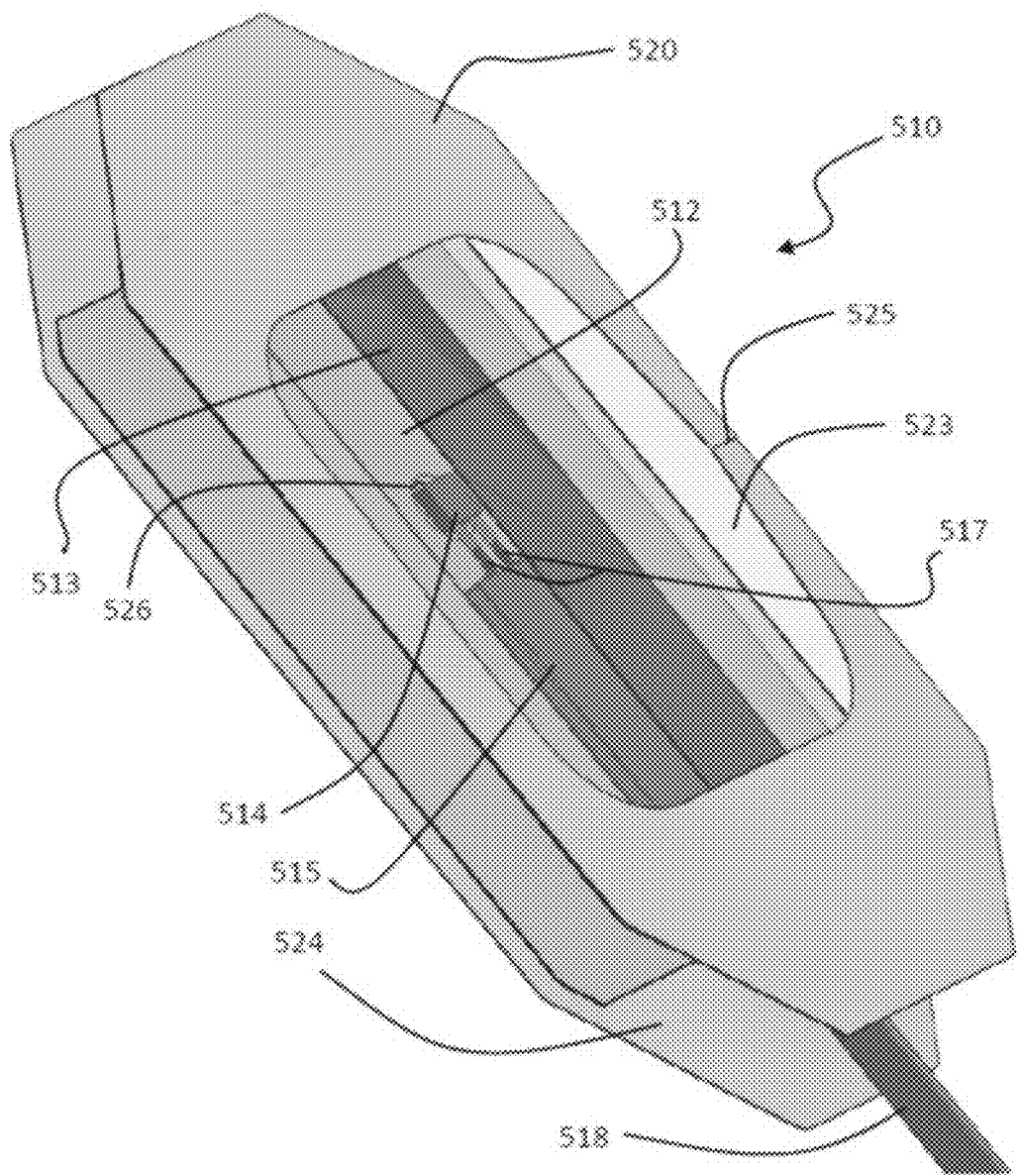
FIG. 7 is a perspective exploded view of the sensor assembly 510 of FIG. 6.
Figure 8:
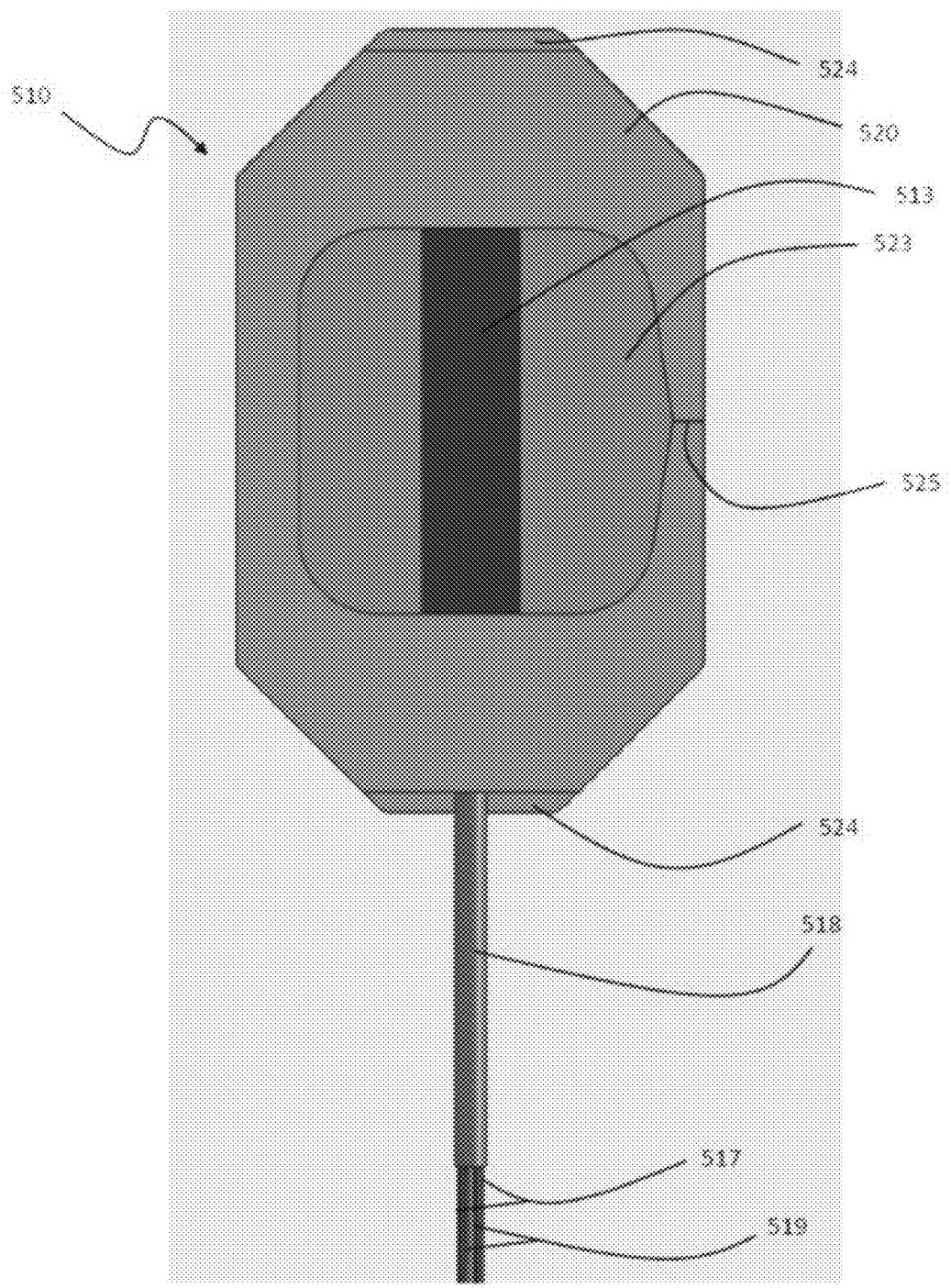
FIG. 8 is another top view (non-transparent) of the embodiment of the sensor assembly shown in FIGS. 6 and 7 showing how the position of the body 512 (covered by an insulator strip 513) can be seen through the clear window 523 in the cover film 520.

A second sensor assembly embodiment will now be described with reference to FIGS. 6-8. This sensor assembly 510 has an elongate body 512 (which is seen only in the exploded view shown in FIG. 7) for supporting a light emitting source 514 (see FIGS. 6 and 7) and a detector 516 (see FIG. 6). The elongate body 512 of this particular embodiment is provided by a length of two-sided tape (tape having adhesive provided on both sides) which enables the body 512 to be fixed on one side to a skin contacting pad 524 (to be discussed below) and to hold in place other components to be described below. The skilled person will recognize that the body 512 may be constructed of materials other than tape and fixed in place by other means which are known to the skilled person.

The LEDs and detectors described with reference to the first embodiment above are suitable for use with this second embodiment. Wires 517 extend from the light emitting source 516 and run alongside wires 519 extending from the detector 516. Both sets of wires 517 and 519 are encased in transmission cable 518. The light emitting source wires 517 provide electrical power to the light emitting source 514. The detector wires 519 provide electrical power to the detector 516 and carry signals obtained by the detector 516 to a signal processor (not shown) when the sensor assembly 510 is in use.

The elongate body 512 has an opening 526 for the light emitting source 514 (see FIGS. 6 and 7) and an opening 528 (which is seen only in FIG. 6) for the detector 516. In this embodiment, the wires 517 and 519 are rigid and rest upon the elongate body 512 where they are held in place by the adhesive of the top surface of the two-sided tape forming the body 512. In certain embodiments, it is advantageous to fix these wires to the elongate body 512 using adhesive or glue. In this arrangement, the light emitting source 514 and the detector 516 are held in place above their respective openings 526 and 528 in the elongate body 512.

Figure 9:
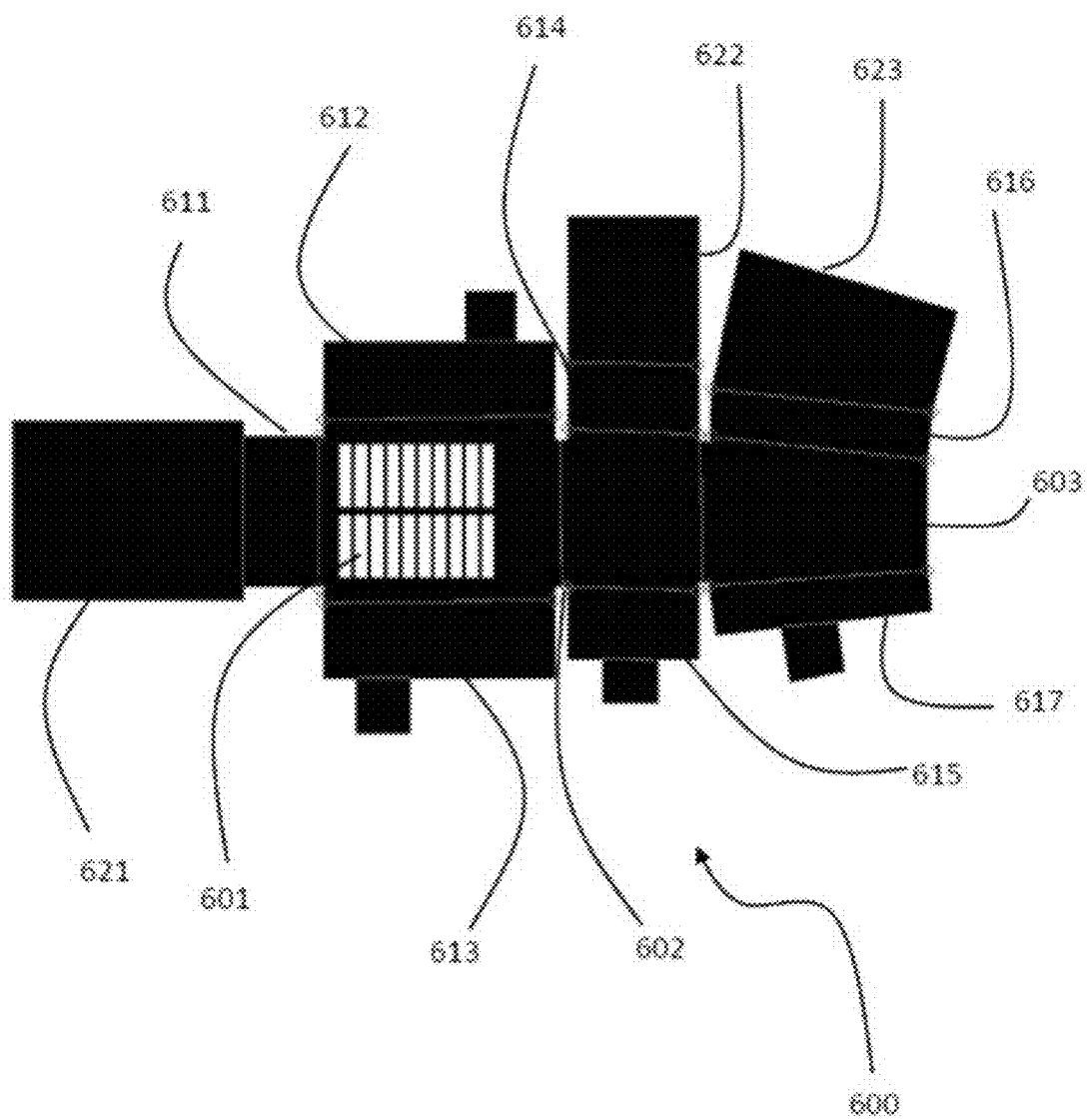
FIG. 9 is a top view of a blank cutout 600 used to form one embodiment of the radiofrequency/electromagnetic interference shield of one embodiment of the sensor assembly 510. The blank includes a first floor section containing a Faraday window 601 and additional panels 602 and 603 for forming floor sections as well as wall panels 611-617 and roof panels 621-623.

In this particular embodiment, the detector 516 is protected from extraneous radiofrequencies and electromagnetic interference by a radiofrequency/electromagnetic interference shield 515 which covers the top and sides of the detector 516. The bottom of the shield 515 includes a Faraday cage window 515F which is seen more clearly in the inset 6' of FIG. 6. The Faraday cage window 515F allows entry of scattered light originating from the light emitting source 514 for access to the detector 516 while preventing entry of radiofrequency and electromagnetic interference. Advantageously, in certain embodiments, the shield 515 is constructed of copper foil and a lead-free solder, such as Kester 331 OA neutral organic water soluble flux lead free solder, is used to make the connections to the cable shield braid as well as to connect the lead wires to the light emitting source 514 and the detector 516. The manner of making electrical connections to components housed within such a shield is well known to the person skilled in the art. A suitable shield blank for forming a shield box according to one embodiment of the present invention is shown in FIG. 9. The shield blank 600 includes three separate panels 601, 602 and 603 for forming the floor of the shield box. Panel 601 is provided with a Faraday cage window as shown. Panels 611-617 form the side walls of the shield box and panels 621, 622 and 623 provide the sections of the ceiling of the shield box.

This embodiment of the sensor assembly 510 includes a skin-contacting film 524. In certain embodiments this film 524 is formed of silicone rubber that forms a high performance elastomeric film. In some embodiments, the material used to form the skin-contacting film 524 as well as the cover film 520 (to be described hereinbelow), is CLS3060 CLR transparent medical grade self-bonding two component silicone rubber which is manufactured by Momentive Inc. of Columbus, Ohio, USA (formerly GE Silicones). This material offers a convenient 1:1 mix ratio, high tensile strength and rapid cure time and may be provided with pigments such as Polyone Stan-Tone 10FSP03 Titanium White or 90FSP06 Iron Oxide Black. These pigments are FDA approved pigments for silicone. The skin-contacting film 524 and the cover film 520 can be prepared by liquid injection molding.

The skin-contacting film 524 is provided with openings that align with openings 526 and 528 for the light emitting source 514 and detector 516, respectively to allow the emitted light to exit the sensor assembly, scatter off various anatomical structures within the hand at the lower half of the palm or the ulnar edge of the palm with differential absorption by oxygenated and deoxygenated blood, followed by impingement upon the detector 516.

In this particular embodiment, the length of the entire elongate body 512 is covered by an insulating strip 513 which serves to cover the light emitting source 514 and the shield 515. In certain embodiments, the insulating strip is an insulating tape such as Kapton® tape which is manufactured by Dupont Inc. Other insulating tapes are known to the skilled person and alternative insulating tapes may be selected for use as an insulating strip by the skilled person without undue experimentation. The insulating strip 513 may also serve to hold the elongate body 512 in place on the skin-contacting film 524. Alternatively, an adhesive may be used to fix the lower surface of the elongate body 512 to the inner surface of the skin-contacting film 524. In other embodiments, both of these features are included. As described above for the first embodiment, additional adhesive films may be provided to hold the transmission cable 518 in place on top of the skin-contacting film 524 in other embodiments (not shown).

The sensor assembly 510 is provided with a cover film 520 as noted above. The cover film 520 has adhesive for fixing it to the skin-contacting film 524 such that both films 520 and 524 overlap substantially with each other and hold the body 512 in a fixed position. In this particular embodiment, the cover film 520 is formed of materials similar to those described above for forming the skin-contacting film 524. In this particular embodiment, the cover film 520 is provided with a transparent window 523 which allows the position of the elongate body 512 to be observed (as indicated by the position of the insulating strip 513). As seen in FIG. 7, the cover film has a transverse fold 525 on the right side of the window 523 which can be pinched to facilitate removal of the backing sheet (not shown) which protects the adhesive layer prior to use. In certain embodiments, both the skin-contacting film 524 and the cover film 520 are provided with backing sheets to protect the adhesive layers of these sheets prior to use, according to the manner which is well known in the art.

Adhesion of the assembly to the skin is provided by the adhesive of the skin-contacting film and the elongate body of the sensor 512, is prevented from moving by adhesion provided by the cover film 520. The sensor assembly 510 of this embodiment can be fixed to an appropriate position on the lower half of the palm or the ulnar edge of the palm as described in detail hereinbelow.

Placement and Operation of the Sensor Assembly

The placement and operation of the sensor assembly of the invention will now be described with reference to FIGS. 10-14. Each placement promotes ease of ambulation and mobility of the patient. The mobility of the hand and flexing of the wrist does not interfere with the sensor or its connection to a signal processing unit. It should be understood that while FIGS. 10-14 make reference to reference numerals of the embodiment of FIGS. 1-5, the sensor assembly embodiment of FIGS. 6-8 (with its reference numbers in the 500 series) may be placed and operated in a similar manner.

In one position, the sensor assembly 10 may be placed at the lower half of the hand (in an orientation wherein the fingertips are at the top) between the center of the palm and the center of the back of the hand. In some embodiments, the sensor may be placed on the ulnar edge of the palm. In other embodiments, the sensor is placed at a distance up to 50% from the ulnar edge of the palm UEP in either transverse direction (toward the palm or toward the back of the hand).

Figure 10:
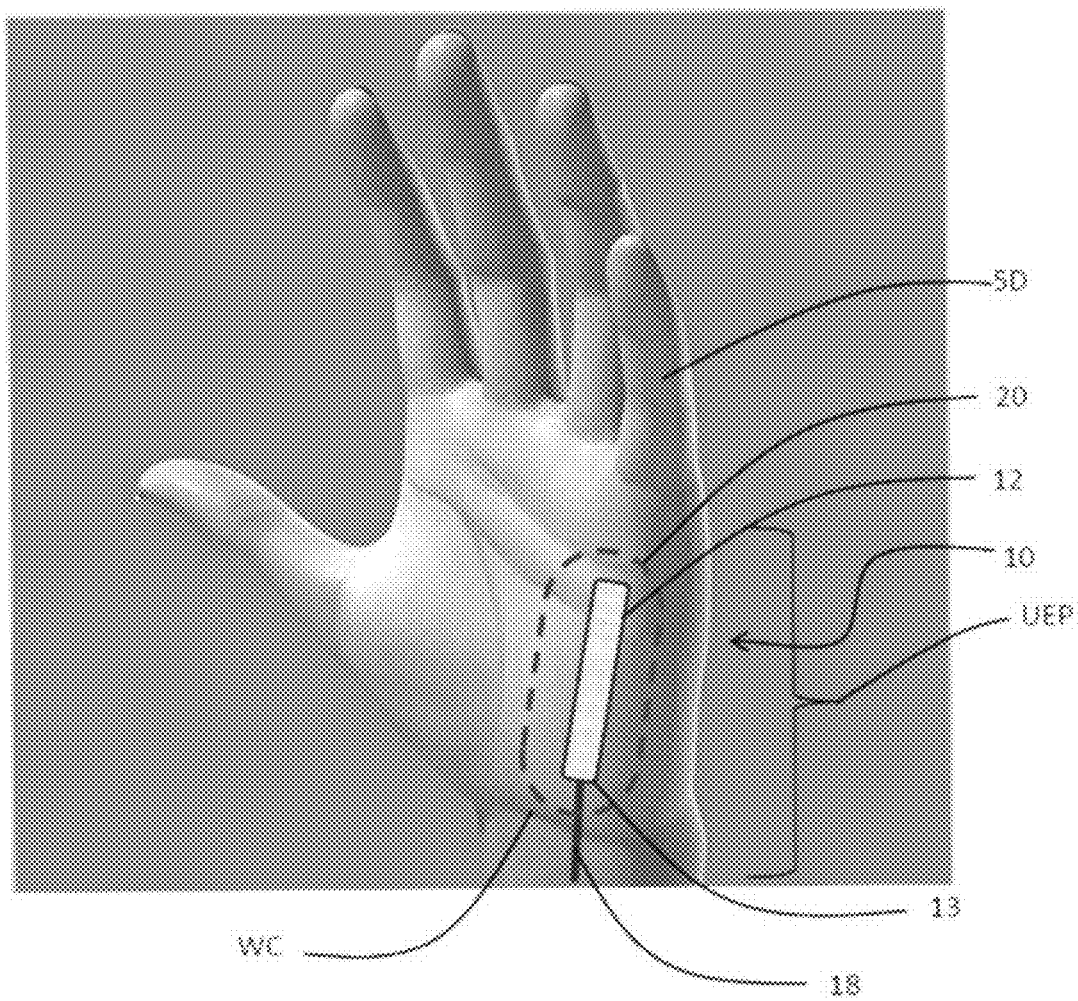
FIG. 10 is a perspective view of a hand with fingers extended showing one possible placement of one embodiment of a sensor assembly 10 on the palmar side of the ulnar edge of the palm UEP generally parallel to the fifth digit 5D and generally orthogonal to the wrist crease WC. Features of the sensor assembly 10 are omitted for clarity.

In one particular embodiment, with reference to FIG. 10, the sensor assembly 10 is attached to the palmar side of the ulnar edge of the palm UEP, along the longitudinal axis formed by the length of the fifth digit and generally orthogonal to the wrist crease WC. Some angling of the sensor assembly 10 with respect to the transverse axis of the wrist crease WC is permitted and the actual angle may vary according to the individual user. This angle may be determined without any undue experimentation or any exercise of any professional skill on the part of the medical practitioner or technician responsible for placing the sensor assembly on an individual for whom pulse oximetry readings are desired. In some cases, the angle may be such that the sensor assembly lies at least partly above the capitate carpal bone. In such cases, the angling of the sensor assembly 10 may cause it to no longer overlap with some of the other carpal bones, such as the pisiform carpal bone, for example. The present inventors have surprisingly discovered that the particular placement shown in FIG. 10 allows the sensor assembly 10 to acquire good signals while also avoiding stable fixation of the sensor assembly 10 at a location that avoids many kinds of incidental movements of a fixed sensor such as wrist flexion, and contact with fingers during gripping of objects in the palm of the hand.

The placement of the sensor assembly 10 on the palmar side of ulnar edge of the palm UEP is shown in FIG. 10. It is seen that the body 12 of the sensor assembly 10 is placed at a position substantially parallel to the longitudinal axis of the fifth digit on the palmar side of the ulnar edge of the palm UEP below the fifth digit 5D and above (and generally orthogonal to) the wrist crease WC. For the sake of clarity, most of the features of the sensor assembly 10 are omitted. An outline of the position of the cover film 20 is shown with a broken line to indicate the approximate location of this feature on the palmar side of the ulnar edge of the palm UEP. The transmission cable 18 is also shown extending from a proximal end 13 of the body 12.

Figure 11:
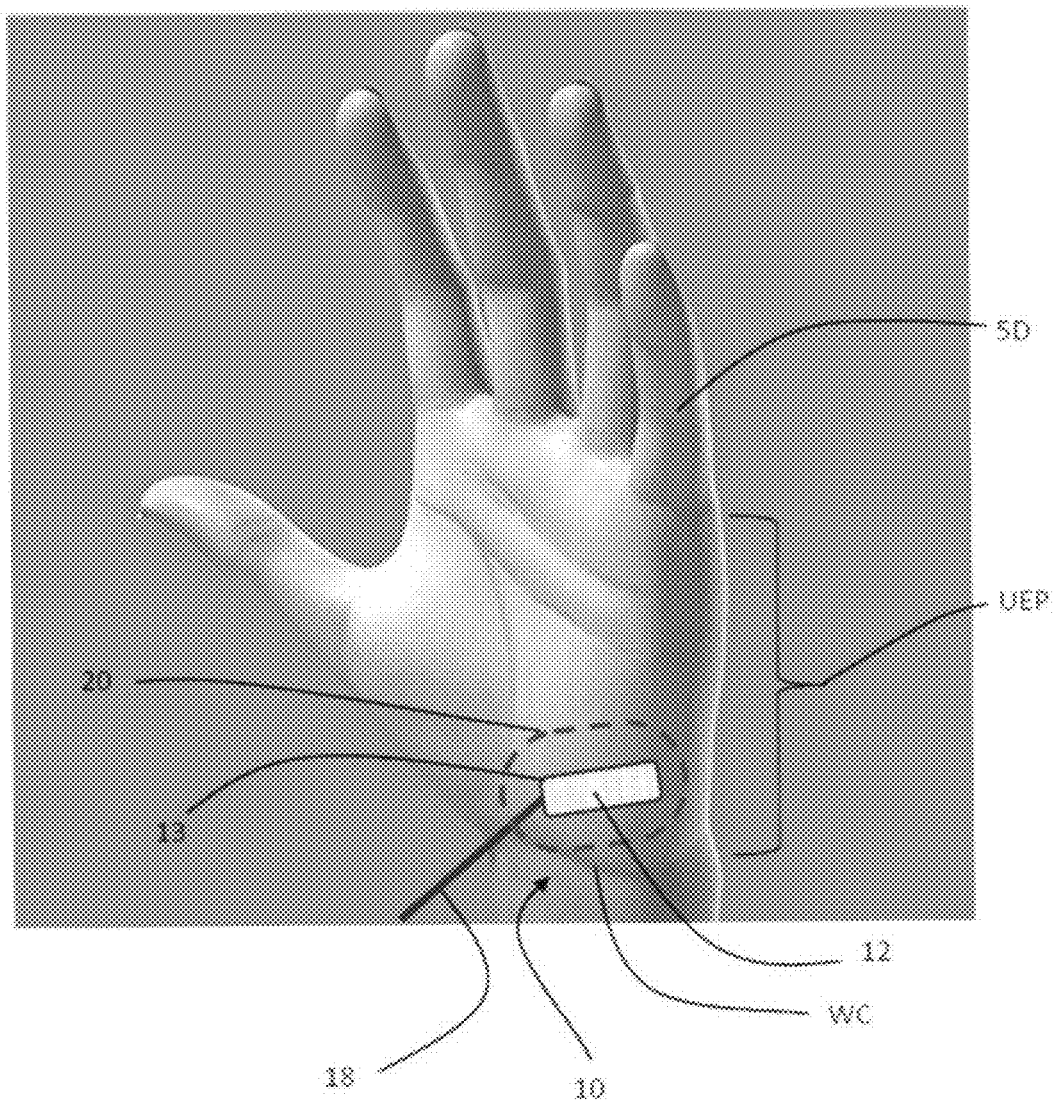
FIG. 11 is a perspective view of a hand with fingers extended showing another possible placement of one embodiment of a sensor assembly 10 on the palmar side of the ulnar edge of the palm UEP generally orthogonal to the fifth digit 5D and generally parallel to the wrist crease WC. Features of the sensor assembly 10 are omitted for clarity.

Another placement of the sensor assembly 10 on the palmar side of the ulnar edge of the palm UEP is shown in FIG. 11. In this placement, the sensor is generally parallel with and overlapping a transverse palmar axis which is generally defined by the pisiform, lunate and scaphoid carpal bones and generally orthogonal to the axes defined by the lengths of the metacarpals (some angling is permitted). In this placement, signals acquired by the sensor assembly 10 during use are not affected by a gripping motion because the fingers, when flexed in a gripping motion do not extend downward far enough to impact the sensor. This reduces the need for extensive signal averaging by the signal processor of the pulse oximetry system.

Figure 12:
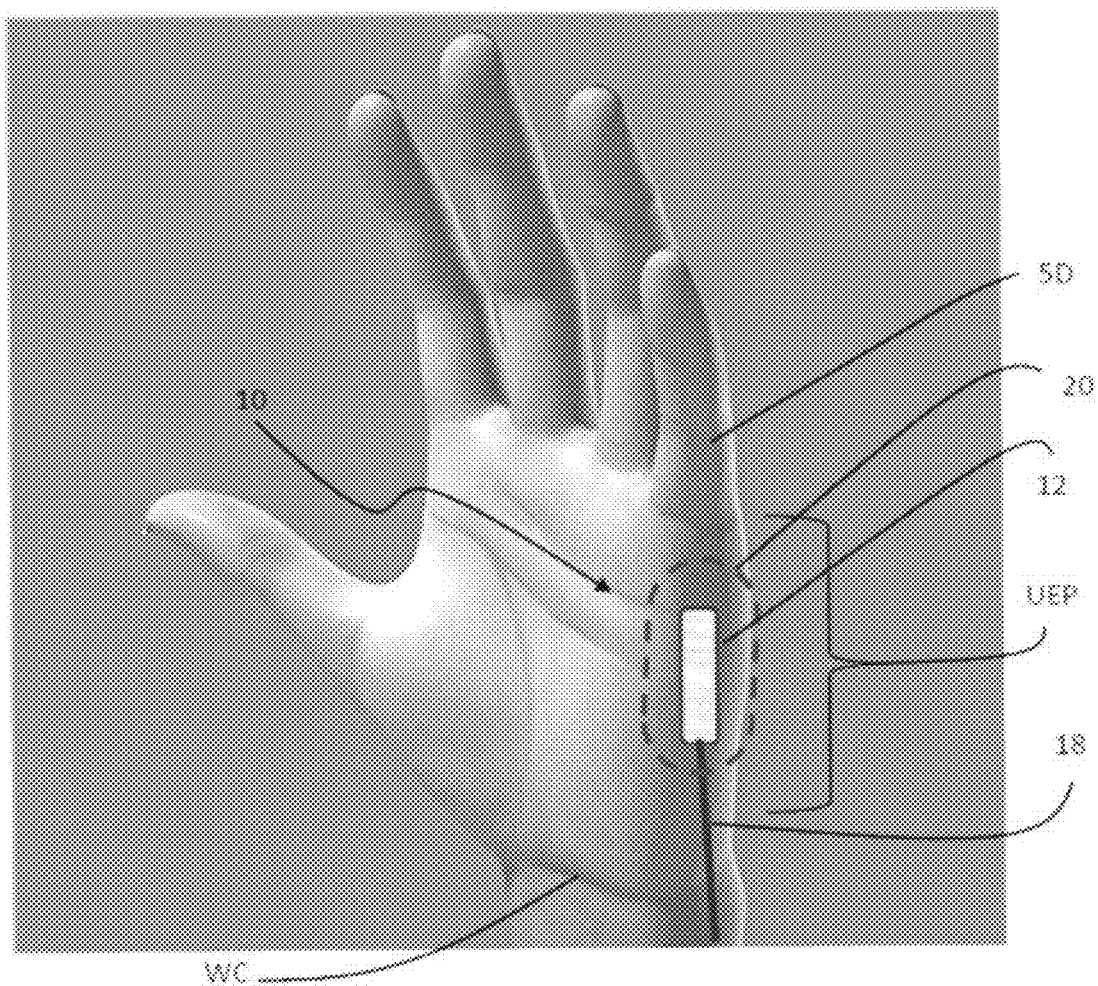
FIG. 12 is a perspective view of a hand with fingers extended showing another possible placement of one embodiment of a sensor assembly 10 on the ulnar edge of the palm UEP generally parallel to the fifth digit 5D and generally orthogonal to the wrist crease WC. Features of the sensor assembly 10 are omitted for clarity.

Another placement of the sensor assembly 10 on the ulnar edge of the palm UEP is shown in FIG. 12. In this placement, the sensor is generally parallel with the fifth digit. In this placement, as for the other placements described above, the signals acquired by the sensor assembly 10 in this placement are not affected by a gripping motion.

Figure 13:
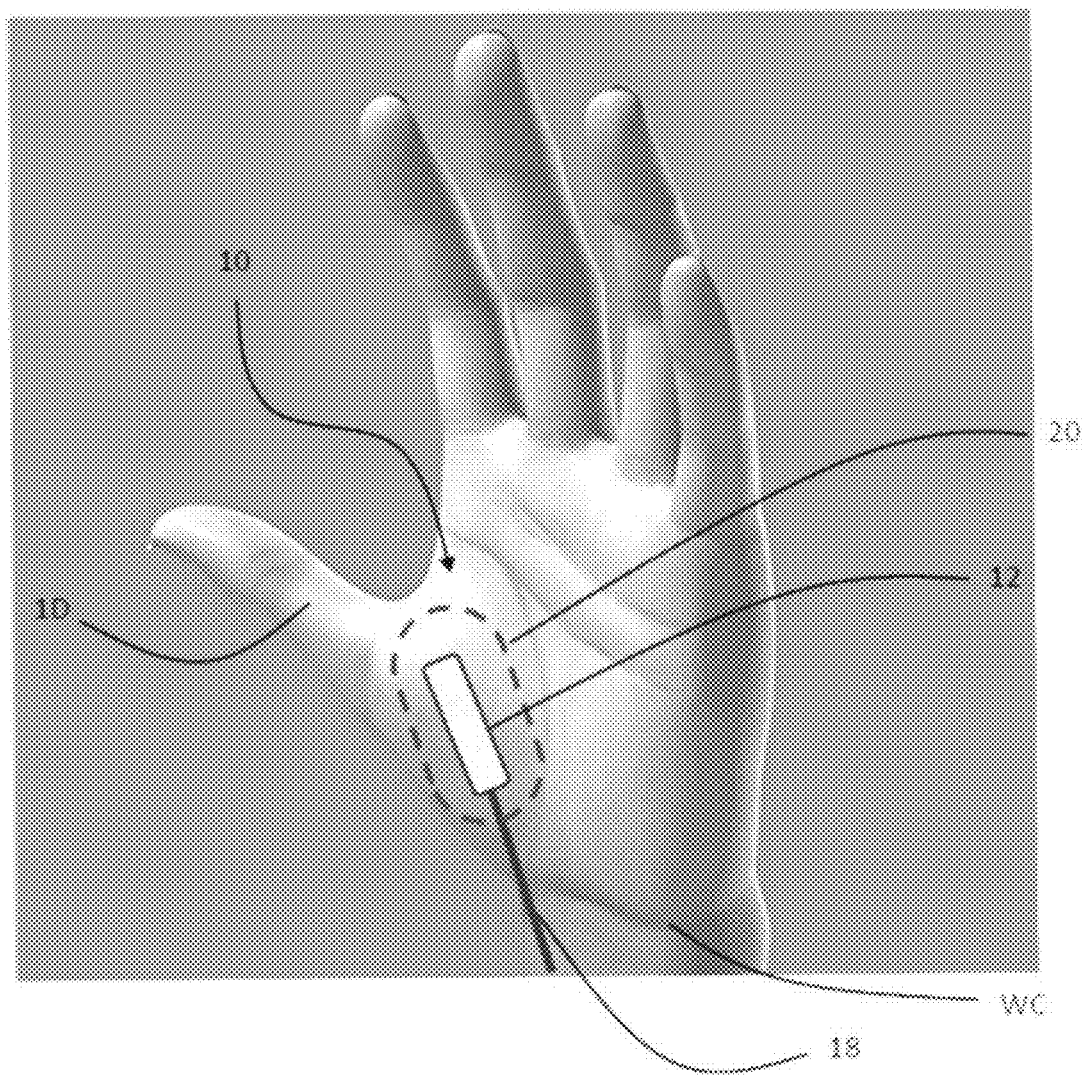
FIG. 13 is a perspective view of a hand with fingers extended showing another possible placement of one embodiment of a sensor assembly 10 above the wrist crease WC along the axis formed by the scaphoid S, and trapezoid Tz carpal bones and the first digit 1D. Features of the sensor assembly 10 are omitted for clarity.

Yet another placement of the sensor assembly 10 is shown in FIG. 13. In this placement, the sensor assembly 10 is attached to the lower half of the palm above the wrist crease WC along the axis formed by the scaphoid S, and trapezoid Tz carpal bones and the first digit 1D. The signals acquired by the sensor assembly 10 in this placement are not affected by a gripping motion.

Figure 14:
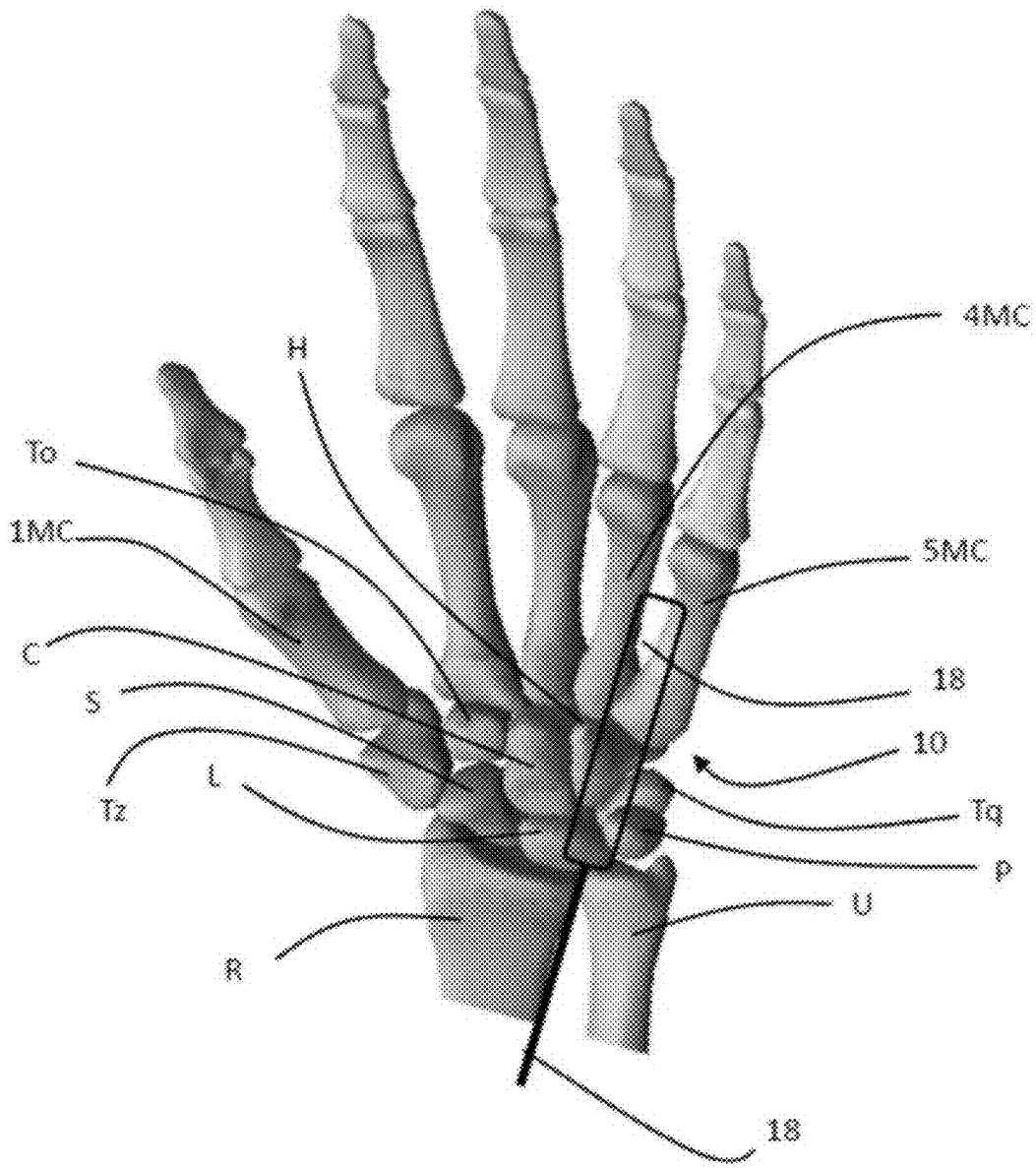
FIG. 14 is perspective view of the skeleton of a hand showing one possible placement of one embodiment of the sensor assembly 10 on the palmar side of the ulnar edge of the palm. It can be seen that the elongate body 12 of the sensor assembly 10 lies opposed to the fifth metacarpal SMC with some overlap of the fourth metacarpal, 4MC, and the hamate H, triquetrum T, lunate L and pisiform P carpal bones.

Shown in FIG. 14 is a view of the skeleton of the palmar side of the left hand which indicates a placement of the main body 12 and transmission cable 18 of the sensor assembly 10 which generally corresponds to the position described for FIG. 10. It can be seen that specific bones of the skeleton of the hand lie beneath the body 12 of the sensor assembly 10. These bones, recited from the top and moving generally downward, are: the fifth metacarpal SMC, the fourth metacarpal 4MC, the first metacarpal 1MC, the hamate H, the capitate C, the trapezoid To, the scaphoid S, the trapezium Tz, the triquetrum Tq, the lunate L, and the pisiform P. Also indicated for context are the radius R and the ulna U. Without being bound by any particular theory, it is believed that light emitted from the light source 14 passes (with some amount of scattering) through soft tissues of the palmar side of the ulnar edge of the palm UEP with partial absorbance by oxygenated and deoxygenated hemoglobin in the blood vessels and with additional scattering from the harder surfaces of the bones described above with subsequent detection by the detector 16. It is this detection of scattered light that forms the basis of the pulse oximetry measurements.

Sensor Systems

Another aspect of the present invention is a system which includes the sensor described herein. Embodiments of such a system are shown in FIGS. 15A and 15B. Features of the sensor have been described above and are omitted from FIGS. 15A and 15B for the sake of clarity. Referring now to FIG. 15A, the sensor assembly 1000 is connected to a monitor 1130 (such as the NELLCOR™ monitor or the MASSIMO™ monitor mentioned above) which processes signals obtained by the detector (not shown) and displays the data. The connection of the sensor assembly 1000 to the monitor 1130 is made by a transmission cable 1080 with plugs 1084 and 1086. In certain embodiments, the plugs are MASSIMO™ plugs as shown in FIG. 16 or NELLCOR™ plugs as shown in FIG. 17. The data acquired by the monitor 1130 may be stored on a local computer workstation 1140, a removable data storage unit 1150 or by an internet connection configured for cloud data storage 1160. An alternative embodiment shown in FIG. 15B is similar to that of FIG. 15A with the exception that the transmission cable 1080 is replaced with a wireless transmission system configured to provide a wireless signal 1170 to the monitor 1130. In this embodiment, the sensor assembly 1000 is provided with a transmitter 1172 to send the wireless signal 1170 and the monitor 1130 is provided with a signal receiver 1174 to receive the signal 1170. Wireless signal systems are commercially available and can be adapted for use with this aspect of the invention, without undue experimentation.

Sensor Kits

Another aspect of the invention is a kit comprising the sensor described herein. Advantageously, the kit includes instructions for attachment of the sensor to the hand. In some embodiments, the instructions specify placement to the lower half of the palm. In other embodiments, instructions for attachment of the sensor to the ulnar edge of the palm are provided. In certain embodiments, the sensor is encased in conveniently removable film to provide a package. Advantageously, the package is sterilized in certain embodiments. The package may be provided with perforated tear lines to facilitate the removal of the sensor from the package without wrinkling of the cover film. The kit may include a skin-contacting film and a cover film, each provided with backing paper to protect the adhesive(s) disposed thereon. The kit may also include a transmission cable configured for attachment to the sensor at one end and to a signal processing unit at the other end.

Methods for Obtaining Pulse Oximetry Readings

Another aspect of the invention is a method for obtaining pulse oximetry readings. The method includes the steps of: attaching a pulse oximetry sensor assembly to the palmar side of the ulnar edge of the palm between the wrist crease and the base of the fifth digit, substantially parallel to a longitudinal axis defined by the fifth digit; connecting the sensor to a signal processing unit; and reading output data from the signal processing unit.

In another embodiment, the method for obtaining pulse oximetry readings includes the steps of attaching a pulse oximetry sensor to the palmar side of the ulnar edge of the palm adjacent the wrist crease and substantially parallel to a transverse axis defined by the pisiform, lunate and scaphoid carpal bones; connecting the sensor to a signal processing unit; and reading output data from the signal processing unit.

Advantageously, the sensor assembly is the pulse oximetry sensor assembly described herein. In certain embodiments, the method further includes the step of storing the output data from the signal processing unit on a computer readable medium.

CONCLUDING STATEMENTS

It is to be understood that the words used in the present description of exemplary embodiments are words of description rather than limitation, and that changes may be made within the purview of the appended claims without departing from the true scope and spirit of the invention in its broader aspects.

While various embodiments of the invention have been particularly shown and described, it will be understood by those skilled in the art that various changes in form and details may be made therein without departing from the spirit and scope of the invention as defined by the appended claims.

All publications, patent applications, patents, internet sites and other references mentioned herein are incorporated by reference in their entirety. In case of conflict, the present specification, including definitions, will control.

What is claimed is:

1. A pulse oximetry sensor assembly configured for attachment to the ulnar edge of the palm, the sensor assembly comprising:
   a) an elongate body comprising:
      a top surface;
      a lower surface;
      a light emitting source; and
      a detector, the detector configured to detect light originating from the light emitting source and scattered from a surface of the ulnar edge of the palm, wherein the detector comprises:
         an interference shield configured to protect the detector from radiofrequency/electromagnetic interference, the interference shield comprising:
            a copper foil; and a Faraday cage window, the Faraday cage window allowing transmission of scattered light to the detector;
b) a skin-contacting film formed of elastomeric material, wherein the skin-contacting film comprises:
a skin-contacting surface comprising an adhesive;
an inner surface, wherein the inner surface is in contact with the elongate body lower surface;
a first opening allowing transmission of light from the light emitting source to the surface of the ulnar edge of the palm; and
a second opening allowing transmission of scattered light from the surface of the ulnar edge of the palm to the detector;
c) an insulating tape comprising an insulating material, wherein the insulating tape is essentially aligned with the elongate body and covers the top surface of the elongate body;
d) a means for transmitting signals acquired by the detector to a signal processing unit, wherein the signals correspond to the scattered light; and
e) a cover film formed of an elastomeric material and covering the insulating tape, elongate body, and skin-contacting film, the cover film comprising:
a transparent window allowing visualization of elongate body and insulating tape placement in relation to the skin-contacting film and/or surface of the ulnar edge of the palm; and
an adhesive to affix the cover film to the insulating tape and skin contacting film.

2. The pulse oximetry sensor assembly of claim 1 wherein the elongate body is between about 30 mm to about 75 mm in length and about 8 mm to about 15 mm in width.

3. The pulse oximetry sensor assembly of claim 1, wherein the distance between the center of the light emitting source and the center of the detector is between about 8 mm to about 10 mm.

4. The pulse oximetry sensor assembly of claim 1, wherein the cover film has a length of about 30 mm to about 75 mm and a width of about 10 mm to about 33 mm.

5. The pulse oximetry sensor assembly of claim 1, wherein the light emitting source is a 600 and 900 nanometer wavelength red/infrared bi-color light emitting diode (LED).

6. The pulse oximetry sensor of claim 1, wherein the means for transmitting signals is a transmission cable in electrical communication with the detector.

7. The pulse oximetry sensor assembly of claim 6 wherein the transmission cable terminates in a plug for connection to a signal processing unit.

8. The pulse oximetry sensor assembly of claim 6, wherein the elongate body, the light emitting source and the detector are disposable and detachable from the transmission cable.

9. The pulse oximetry sensor assembly of claim 1, wherein the means for transmitting is a wireless signal transmission system comprising a wireless transmitter in data transfer communication with the detector and a wireless receiver in data transfer communication with the signal processing unit.

10. The pulse oximetry sensor assembly of claim 1, wherein the cover film extends outward from the skin contacting film to provide adhesion to skin of a palm, thereby holding the pulse oximetry sensor assembly in place on the ulnar edge of a palm when the sensor is in use.

11. A pulse oximetry system comprising:
a) the pulse oximetry sensor assembly of claim 1, wherein the means for transmitting signals acquired by the detector comprises a transmission cable, wherein the transmission cable is in electrical communication with the detector; and
b) a signal processing unit in electrical communication with a display unit for displaying pulse oximetry readings.

12. The pulse oximetry system of claim 11, wherein the signal processing unit is in data transfer communication with a computer readable medium for storage of the pulse oximetry readings.

13. The pulse oximetry system of claim 11 wherein the transmission cable is detachable from the sensor and the sensor is disposable.

* * * * *